(12) United States Patent
Paci et al.

(10) Patent No.: US 10,098,901 B2
(45) Date of Patent: Oct. 16, 2018

(54) DERIVATIVES OF OXAZAPHOSPHORINES AND THERAPEUTIC USES THEREOF

(71) Applicant: INSTITUT GUSTAVE ROUSSY, Villejuif (FR)

(72) Inventors: Angelo Paci, Meudon (FR); Thierry Martens, La Queue en Brie (FR); Michael Rivard, Creteil (FR); Didier Desmaele, Fresnes (FR); Charles Skarbek, Paris (FR); Patrick Couvreur, Villebon sur Yvette (FR)

(73) Assignee: INSTITUT GUSTAVE ROUSSY, Villejuif (FR)

( * ) Notice: Subject to any disclaimer, the term of this patent is extended or adjusted under 35 U.S.C. 154(b) by 0 days.

(21) Appl. No.: 15/310,455

(22) PCT Filed: May 13, 2015

(86) PCT No.: PCT/EP2015/060706
§ 371 (c)(1),
(2) Date: Nov. 11, 2016

(87) PCT Pub. No.: WO2015/173367
PCT Pub. Date: Nov. 19, 2015

(65) Prior Publication Data
US 2017/0071959 A1    Mar. 16, 2017

(30) Foreign Application Priority Data

May 14, 2014 (EP) .................................... 14305703

(51) Int. Cl.
*A61K 31/664* (2006.01)
*A61K 31/185* (2006.01)
*C07F 9/6584* (2006.01)
*A61K 47/48* (2006.01)

(52) U.S. Cl.
CPC .......... *A61K 31/664* (2013.01); *A61K 31/185* (2013.01); *A61K 47/48023* (2013.01); *C07F 9/65846* (2013.01)

(58) Field of Classification Search
CPC ................ A61K 31/664; A61K 31/185; A61K 47/48023; C07F 9/65846
USPC .......................................... 558/80
See application file for complete search history.

(56) References Cited

U.S. PATENT DOCUMENTS 9,073,957 B2    7/2015  Paci et al.
2013/0261088 A1  10/2013  Paci et al.

FOREIGN PATENT DOCUMENTS

WO    WO 2012/076824    6/2012

OTHER PUBLICATIONS

Written Opinion in International Application No. PCT/EP2015/060706, dated Jun. 24, 2015, pp. 1-6.

*Primary Examiner* — Kristin A Vajda
(74) *Attorney, Agent, or Firm* — Saliwanchik, Lloyd & Eisenschenk (57) ABSTRACT

The present invention relates to novel derivatives of oxazaphosphorines, pharmaceutical compositions and therapeutic uses thereof, in particular for treating or preventing cancer.

3 Claims, 5 Drawing Sheets

DERIVATIVES OF OXAZAPHOSPHORINES AND THERAPEUTIC USES THEREOF

CROSS-REFERENCE TO RELATED APPLICATION

This application is the U.S. national stage application of International Patent Application No. PCT/EP2015/060706, filed May 13, 2015.

The present invention relates to novel derivatives of oxazaphorines useful for the treatment of cancers.

BACKGROUND OF THE INVENTION

Figure 5:
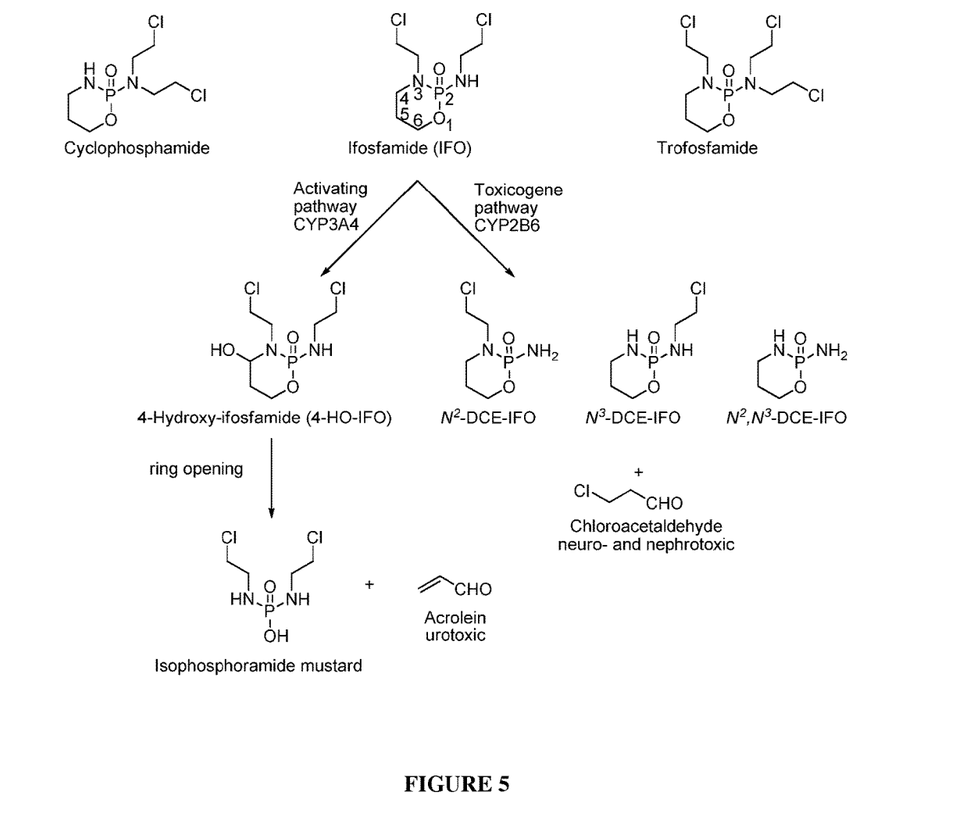
FIG. 5 shows the chemical structure of cyclophosphamide, ifosfamide (IFO) and trofosfamide as well as the metabolism of IFO in vivo.

Oxazaphosphorines belong to alkylating agents that have been widely used in routine clinical practices to treat several types of cancer from soft tissue tumor to lymphoma. Oxazaphosphorines include ifosfamide (IFO), cyclophosphamide (CPM) and trofosfamide, which have an isomeric structure containing one, two or three chloroethyl groups bound to the nitrogen atoms. As prodrugs, these compounds require a metabolic activation fulfilled by specific liver cytochrome P450 (CYP). This activation produces hydroxylated intermediates which by a ring opening mechanism liberate the active drug, namely the nitrogen mustard which displays cytotoxicity by DNA crosslinks. The main activation pathway of IFO is carried out by CYP3A4 and involves an oxidation reaction on the C-4 carbon atom, leading to 4-hydroxy-ifosfamide (4-HO-IFO). 4-HO-IFO gives rise to the alkylating mustard concomitantly with acrolein through tautomeric equilibrium and retro-Michael process. Acrolein is responsible for the urological toxicity characterized by hemorrhagic cystitis. Acrolein-related toxicity can be attenuated by co-administration of sodium mercaptoethanesulfonate. In addition, oxazaphosphorines may also cause neurotoxicity and nephrotoxicity due to the release of chloroacetaldehyde, a metabolite produced by oxidation of the side chains of the molecules via the action of cytochrome, in particular CYP2B6 (see FIG. 5).

To circumvent these toxicities, pharmacomodulation of oxazaphosphorines has been investigated. Chemical oxidation of the C-4 carbon center has been proposed in order to provide pre-activated analogues able to release the alkylating mustards without undergoing metabolization by cytochrome P450. Many derivatives have already been prepared such as 4-methoxy derivatives (Paci et al., 2001, Bioorg Med Chem Lett, 11, 1347-1349) but most of them were either found too unstable for further development or had no advantage over the use of IFO.

WO2012/076824 discloses ifosfamide derivatives SQ-IFO and SQ-thio-IFO, which comprises a squalenoyl radical at C-4 carbon. These compounds were shown to display cytotoxicity on several cancerous cells and to be able to self-organize into nanoparticles thanks to its long hydrophobic tail. However, squalenoyl derivatives are not easily accessible and their preparation may require the use of toxic reagents, which are generally precluded from the synthesis of active ingredients to be used in medicine.

There is still a need for new derivatives of oxazaphosphorines for the treatment of cancers.

SUMMARY OF THE INVENTION

In a first aspect, the invention relates to a compound of formula (I):

wherein:

A is O, S, —NH— or a spacer moiety having a molecular weight up to 500 g·mol$^{-1}$, $R_1$, $R_2$ and $R_3$ are independently selected from the group consisting of —H, —CH(CH$_3$)—CH$_2$—X and —(CH$_2$)$_2$—X, X being an halogen atom, preferably selected among Cl, Br or I, or a pharmaceutically acceptable salt or solvate thereof.

In some embodiments, at least two among $R_1$, $R_2$ and $R_3$ are independently selected from —CH(CH$_3$)—CH$_2$—X and —(CH$_2$)$_2$—X.

In some additional embodiments, A is a spacer selected from the group consisting of:

amino acids, dipeptides, and derivatives thereof polyether groups, such as polyethylene glycol or polypropylene glycol, preferably comprising from 2 to 6 monomers;

hydrazone linkers; and combinations thereof.

In other embodiments, the compound of formula (I) is such that A is selected from the group consisting of:

O, S, —O—(C=S)—S—, —ONH—, —O—NR'—, —NHO—, $Y_1$—(CH$_2$)$_n$—$Y_2$, with n is an integer from 1 to 8, preferably from 1 to 6 or from 1 to 4, and $Y_1$—(CH$_2$—CH$_2$—O)$_a$—CH$_2$—CH$_2$—$Y_2$ with a is an integer from 1 to 5, wherein $Y_1$ and $Y_2$ are independently selected from —O—, —NH—, —S—, —OC(O)—, —C(O)NH—, —NHC(O)—, —O—C(S)—S—, S—C(S)—O—NR'—, —ONH—, —NHO—, —ONR'—, —NR'O—, —OC(O)—O—, NR'C(S)S—, —SC(S)NR'—, —NR'C(O)—, —C(O)NR'— and —C(O)O— wherein R' is an alkyl, such as a $C_1$-$C_6$ alkyl, preferably a $C_1$-$C_3$ alkyl.

In some other additional or alternative embodiments, the compound of formula (I) is such that:

$R_2$ is H, and $R_3$ and $R_1$ are —CH(CH$_3$)—CH$_2$—X or —(CH$_2$)$_2$—X, preferably with X=Cl or Br.

Preferably, the compound is (IIb)

or a pharmaceutically acceptable salt thereof.

The compound of the invention may be used as a drug, preferably as an immunosuppressive agent or as an anticancer drug. Accordingly, the invention also relates to the use of a compound of formula (I) in the treatment or the prevention of cancer, preferably in the treatment of cancer.

The cancer may be selected from the group consisting of sarcomas such as osteosarcoma, soft tissue sarcoma and pediatric soft tissue sarcoma, breast cancer, genitourinary cancers such as cancers of prostate, bladder, testis, uterine cervix or ovaries, and lung cancer such as non-small-cell lung carcinoma and small-cell lung carcinoma.

The compound of the invention may be administered by intravenous route or oral route. In some embodiments, the compound of the invention is to be administered in combination with sodium mercaptoethanesulfonate (mesna) and/or with an additional anticancer agent. In some further embodiments, the compound of the invention is formulated as a nanoparticle.

In a further aspect, the invention relates to a nanoparticle formed by a compound of the invention. A further object of the invention is a pharmaceutical composition comprising a compound of formula (I), said compound being optionally formulated as a nanoparticle, and a pharmaceutically acceptable excipient.

DETAILED DESCRIPTION OF THE INVENTION

The present invention relates to new derivatives of oxazaphosphorines comprising a geranyl radical at position C-4. The Applicant showed that such derivatives are able to release the corresponding alkylating mustard without preliminary activation by cytochromes. These compounds may thus display a good therapeutic activity in vivo with reduced neurological and nephrological adverse effects observed for the corresponding oxazaphosphorine.

In particular, the Applicant showed that geranyloxy-IFO is able to self-organize into nanoparticles in spite of its short lipophilic tail. Noteworthy, geranyloxy-IFO displayed cytotoxicity toward cancerous cell lines such as A673 and RMS-1, in the absence of cytochrome. Surprisingly, the cytotoxicity of Geranyloxy-IFO is significantly increased (20-fold) when formulated as nanoparticles as compared to bulk form. By contrast, 13,17-Dimethyloctyloxy-IFO did not provide any suspension of nanoparticles and displayed a poor cytotoxicity activity on cancerous cell lines after an incubation of 72 hours.

Moreover, geranyloxy-IFO was also shown to prevent the tumor growth in a murine model of rhabdomyosarcoma (RD cell tumor xenografted in nude mice). Pharmacokinetics data further showed that, when administered by intravenous route in mice, geranyloxy-IFO was rapidly and mostly converted into the 4-hydroxy-ifosfamide (4-HO-IFO) metabolite which spontaneously releases the alkylating mustard. The conversion of geranyloxy-IFO into inactive N-dechlorethyl metabolites, and thus the release of neuro- and nephrotoxic chloroacetaldehyde, was lower than those observed for IFO. Such a result illustrates that contrary to IFO, geranyloxy-IFO is not significantly metabolized by CYP2B6.

Thus, a first object according to the invention is a derivative of oxazaphosphorines comprising a geranyl radical.

As used herein, the geranyl radical refers to any radical derived from geraniol ((trans)-3,7-dimethyl-2,6-octadien-1-ol) such as:

In some embodiments, the present invention relates to a compound of formula (I):

wherein:

A is O, S, NH, NR' with R' is an alkyl group, preferably a $C_1$-$C_3$ alkyl group, or a spacer group preferably having a molecular weight up to 500 g·mol$^{-1}$, $R_1$, $R_2$ and $R_3$ are independently selected from the group consisting of —H, —CH(CH$_3$)—CH$_2$—X and —(CH$_2$)$_2$—X, wherein X is a halogen atom, preferably Br or I, and more preferably Br or I or a pharmaceutically acceptable salt or solvate thereof.

As used herein, a spacer refers to a chemical moiety linking the geranyl radical to the C-4 atom of oxazaphosphorine. The spacer (also called "linker") may be of any type. For instance, the spacer may comprise, or may consist of, a moiety selected from the group consisting of:

amino acids and derivatives thereof peptides comprising from 2 to 10, preferably from 2 to 5 amino acids and derivatives thereof;

—N(R')— with R' being an alkyl group, in particular a $C_1$-$C_3$ alkyl $C_1$-$C_{10}$ hydrocarbon chains optionally substituted by one or several substituents selected from —OH, $C_1$-$C_4$ alkyl and $C_1$-$C_4$ alkyloxy groups, and/or optionally comprising:

one or several heteroatoms such as S and O; and/or one or several chemical groups such as —NHC(O)—, —OC(O)—, OC(O)O, —NH—, —NH—C(O)—NH—, —S—S—, and —CR"=N—NH—C(O)—, —ONH—, —ONR'—, —O—C(=S)—S—, —C(=S)—S—, and/or one or several heteroaryl or aryl groups, and/or one or several aliphatic cycles or heterocycles, preferably comprising from 4 to 6 atoms, and optionally substituted by one or several substituents selected from —OH, $C_1$-$C_4$ alkyl and $C_1$-$C_4$ alkyloxy groups, wherein R" is H, an aryl group, or an alkyl group such as a $C_1$-$C_6$ alkyl group, preferably a $C_1$-$C_3$ alkyl group, and R' is an alkyl group such as a $C_1$-$C_6$ alkyl group, in particular a $C_1$-$C_3$ alkyl group.

In particular, the spacer may be selected from the group consisting of:

amino acids and derivatives thereof;

peptides comprising from 2 to 10, preferably from 2 to 5 amino acids and derivatives thereof;

$C_1$-$C_{10}$ hydrocarbon chains optionally comprising one or several heteroatoms such as S and O, and/or one or several chemical groups such as —NHC(O)—, —OC(O)—, —NH—, —NH—C(O)—NH—, —S—S—, and —CH=N—NH—C(O)— and/or one or several heteroaryl or aryl groups, said hydrocarbon chains being optionally substituted by one or several substituents selected from —OH, $C_1$-$C_4$ alkyl and $C_1$-$C_4$ alkoxy groups; and combinations thereof.

As used herein, an "Aryl" group refers to an unsubstituted or substituted aromatic ring. Preferably, the aryl group is a phenyl group optionally substituted by one or several groups such as $C_1$-$C_4$ alkyl, $C_1$-$C_4$ alkyloxy, OH or halogen atoms.

As used herein, a "Heteroaryl" refers to an aromatic ring system wherein one or several aromatic atom are a heteroatom such as N, O or S. The heteroaryl group may be substituted or unsubstituted and preferably comprises from 4 to 6 cyclic atoms. Examples of heteroaryl groups are, without being limited to, pyridinyl, pyridazinyl, pyrimidyl, pyrazyl triazinyl, pyrrolyl, pyrazolyl, imidazolyl, triazolyl, pyrazinyl, pyrimidinyl, tetrazolyl, furyl, thienyl, isoxazolyl, thiazolyl, oxazolyl or isoxazolyl groups.

As used herein, an aliphatic "Heterocycles" refers to a non-aromatic ring system wherein one or several aromatic atom are a heteroatom such as N, O or S. The heteroaryl group may be substituted or unsubstituted and preferably comprises from 4 to 6 cyclic atoms. Examples of aliphatic heterocycles are, without being limited to, morpholine, piperazine, pyrrolidine, dioxane, piperidine, tetrahydrofuran and the like.

As used herein, $C_1$-$C_4$ alkyl groups encompass methyl, ethyl, propyl and butyl groups.

As used herein, the term of "pharmaceutically acceptable" refers to compositions, compounds, salts and the like that are, within the scope of sound medical judgment, suitable for contact with the tissues of the subject, or which can be administered to the subject, without excessive toxicity or other complications commensurate with a reasonable benefit/risk ratio.

As used herein, the term "solvate" or "pharmaceutically acceptable solvate" refers to a solvate formed from the association of one or more molecules of compounds of the invention with one or more molecules of solvent. The term solvates include hydrates such as hemi-hydrate, monohydrate, dihydrate, trihydrate, tetrahydrate and the like.

As used herein, the term "pharmaceutically acceptable salt" refers to non-toxic salts, which can generally be prepared by contacting the compound of the invention with a suitable organic or inorganic acid. For instance, pharmaceutical salts may be, without being limited to, acetates, benzenesulfonates, benzonates, bicarbonates, bisulfates, bitartrates, bromides, butyrates, carbonates, chlorides, citrates, diphosphates, fumarates, iodides, lactates, laurates, malates, maleates, mandelates, mesylates, oleates, oxalates, palmitates, phosphates, propionates, succinates, sulfates, tartrates, and the like.

In some embodiments, the spacer is selected among amino acids, dipeptides and derivatives thereof. For instance, the spacer may be based on citrulline, lysine, ornithine, alanine, phenylalanine, cysteine, glycine, valine, leucine and dipeptides thereof. As an example of dipeptide linker, one may cite valine-citrulline linker.

In some other embodiments, the spacer may be a hydrocarbon chain as described above. For instance, the spacer may be a polyether group, such as polyethylene glycol or polypropylene glycol, preferably comprising from 2 to 6 monomers. Alternatively, the spacer may be a hydrazone linker.

In some other embodiments, A is selected from NH, O, S, NR', ONH, ONR', OC(O)O, OC(S)S, N(R')C(S)S—, and their combinations with polyether groups such as polyethylene glycol or polypropylene glycol, preferably comprising from 2 to 6 monomers, wherein R' is an alkyl, preferably a $C_1$-$C_3$ alkyl.

In some embodiments, the spacer may be $Y_1$—(CH$_2$)$_n$—$Y_2$, with n being an integer from 1 to 8, or $Y_1$—(CH$_2$—CH$_2$—O)$_a$—CH$_2$—CH$_2$—$Y_2$ with a being an integer from 1 to 5, wherein $Y_1$ and $Y_2$ are independently selected from —O—, —NH—, —S—, —OC(O)—, —C(O)NR'—, —C(O)NH—, —NHC(O)—, —O—C(S)—S—, —ONH—, —OC(O)—O—, NR'C(S)S—, and —C(O)O—, with R' being an alkyl, preferably $C_1$-$C_3$ alkyl.

In a particular embodiment, the spacer may be $Y_1$—(CH$_2$)$_n$—$Y_2$ wherein n is an integer from 1 to 6, preferably from 1 to 4 and $Y_1$ and $Y_2$ are independently selected from —O—, —NH—, —S—, —OC(O)—, —C(O)NH—, —NHC(O)—, and —C(O)O—.

In some additional embodiments, A is selected from the group consisting of O, S, —NH— and cysteamine linker (i.e. —C(O)NH—CH$_2$—CH$_2$—S—), valine-citrulline linker and cysteine linker. Appropriate spacers according to the invention also encompass:

wherein m is an integer from 0 to 9 and R″ is H or an alkyl group, such as a $C_1$-$C_6$ alkyl, preferably a $C_1$-$C_3$ alkyl group.

Other examples of appropriate spacers consist of or comprise one of the following moieties:

wherein p is an integer from 0 to 4, preferably 1 and R″ is H or an alkyl group, such as a $C_1$-$C_6$ alkyl, preferably a $C_1$-$C_3$ alkyl group.

In some alternate or additional embodiments, at least two groups among $R_1$, $R_2$ and $R_3$ are independently selected from —CH(CH$_3$)—CH$_2$—X and —(CH$_2$)$_2$—X and the remaining group is —H. In some other embodiments, $R_1$, $R_2$ and $R_3$ are independently selected from —CH(CH$_3$)—CH$_2$—X and —(CH$_2$)$_2$—X.

In some additional embodiments, $R_1$, $R_2$ and $R_3$ are independently selected among H and —(CH$_2$)$_2$—X.

In some more specific embodiments, the compound of the invention has one of the following formula (Ia), (Ib) or (Ic):

(Ia)

(Ib)

(Ic)

wherein X and A are as defined for formula (I) and $R_4$, $R_5$ and $R_6$ are independently selected from H or CH$_3$.

In some embodiments, the compound of the invention is selected from the group consisting of:
- a compound of formula (Ia) wherein $R_4$=$R_5$=H,
- a compound of formula (Ia) wherein $R_4$=$R_5$=CH$_3$,
- a compound of formula (Ib) wherein $R_4$=$R_5$=H,
- a compound of formula (Ib) wherein $R_4$=$R_5$=CH$_3$,
- a compound of formula (Ic) wherein $R_4$=$R_5$=$R_6$=H and
- a compound of formula (Ic) wherein $R_4$=$R_5$=$R_6$=CH$_3$.

Preferably, X is Br or Cl and/or A is O, S or —$Y_1$—(CH$_2$)$_n$—$Y_2$ as defined in formula (I), more preferably O or S.

Preferred compounds according to the invention are compounds of formula (Ia) such as:

(IIa)

(IIb)

Other compounds of interest according to the invention are:

Methods for preparing a compound of formula (I) are well-known. The skilled artisan may refer to standard procedures. General protocols for preparing the compounds of the invention are provided in the Examples of the instant application. The skilled artisan may also adapt anyone of the synthetic methods described in WO2012/076824.

The compounds according to the invention are able to self-organize into nanoparticles. Said self-assembly into nanoparticles may increase the biological activity of the compound such as its cytotoxicity and improve its delivery to cancerous cells. Moreover, the compound of the invention in nanoparticle form may have an improved stability as compared to its free form under storage. In some embodiments, the compound of the invention is in the form of nanoparticles.

A further object of the invention is a nanoparticle comprising a compound of the invention. More precisely, a compound of the invention is present as a constituent, more preferably as the main component of the nanoparticle, which means that the compound of the invention may account for more than 50% in weight, e.g. more than 60%, 70%, 80%, 90%, 95%, 98%, 99%, or 99.5% in weight of the total weight of the nanoparticle. In some embodiments, the nanoparticle is formed by a compound of the invention. In other words, the nanoparticle results from the self-organization of molecules of the compound of the invention.

The mean hydrodynamic diameter of the nanoparticle of the invention is typically from 10 to 800 nm, preferably from 30 to 500 nm and in particular from 50 to 400 nm. For instance, the nanoparticles may have a mean hydrodynamic diameter from 70 nm to 200 nm, for instance from 100 nm to 250 nm. The mean hydrodynamic diameter is preferably determined by Dynamic Light scattering at 20° C., for instance by using a Nanosizer ZS (Malvern Instrument Ltd, France) as described in the Examples of the instant patent application.

The nanoparticles of a compound of formula (I) can be obtained by dissolving the compound in an organic solvent such as acetone or ethanol, then adding this mixture into an aqueous phase under stirring leading to the formation of nanoparticles with or without surfactant(s). Surfactants include, for example, polyoxyethylene-polyoxypropylene copolymers, sodium lauryl sulfate, phospholipid derivatives and lipophilic derivatives of polyethylene glycol.

The invention also relates to a colloidal system containing the particles of the invention, preferably in an aqueous medium.

The compound of formula (I), the nanoparticle of the invention as well as any particular compound disclosed herein may be used as a drug, in particular as an immunosuppressive agent or as an anticancer drug.

Thus, a further aspect of the invention is the use of a compound or a nanoparticle of the invention in the treatment or the prevention of cancer.

The invention also relates to a method for treating or preventing a cancer in a subject, said method comprising administering the subject with a therapeutically effective amount of a compound of formula (I) or a nanoparticle as defined above.

The present invention further relates to a method for treating a subject in need of immunosuppression, the method comprising administering the subject with a therapeutically effective amount of a compound of formula (I) or a nanoparticle such as defined above.

As used herein, the term "cancer" refers to a disorder in mammals involving upregulated cell growth and characterized by malignancy. The cancer may be of any type. It may be a solid tumor or a hematopoietic cancer. Preferably, the cancer is selected from the group consisting of carcinoma, sarcoma, lymphoma, leukemia, germ cell tumor, blastoma and melanoma. For instance, the cancer may be selected from, without being limited to, chronic myeloid leukemia, acute lymphoblastic leukemia, Philadelphia chromosome positive acute lymphoblastic leukemia (Ph+ ALL), Hodgkin's disease, Hodgkin's and non-Hodgkin lymphomas, squamous cell carcinoma, small-cell lung cancer, non-small cell lung cancer, glioma, gastrointestinal cancer, renal cancer, ovarian cancer, liver cancer, colorectal cancer, endometrial cancer, kidney cancer, prostate cancer, thyroid cancer, neuroblastoma, pancreatic cancer, glioblastoma multiforme, cervical cancer, stomach cancer, bladder cancer, malignant hepatoma, breast cancer, colon carcinoma, head and neck cancer, gastric cancer, germ cell tumor, pediatric sarcoma, rhabdomyosarcoma, Ewing's sarcoma, osteosarcoma, soft tissue sarcoma, sinonasal NK/T-cell lymphomas, myelomas, melanomas, multiple myeloma, acute myelogenous leukemia (AML), or chronic lymphocytic leukemia.

In some preferred embodiments, the cancer can be selected from the group consisting of chronic leukemias, acute lymphocytic leukemias, Hodgkin's disease, Hodgkin's and non-Hodgkin lymphomas, cancers of the lung, breast cancer, genitourinary cancers such as cancers of prostate, bladder, testis, uterine cervix or ovaries, sarcomas such as osteosarcoma and soft tissue sarcoma including pediatric soft tissue sarcoma, neuroblastomas, myelomas, and melanomas.

More preferably, the cancer is selected from sarcomas including osteosarcoma and soft tissue sarcoma, breast cancer, genitourinary cancers and lung cancer including non-small-cell lung carcinoma and small-cell lung carcinoma.

As used herein, the "treatment of cancer" or "treating cancer" includes curing, delaying, alleviating or slowing the progression of the cancer or that of one or more of the associated symptoms as well as the prevention, the attenuation, the slowing, the reverse or the elimination one or more of the symptoms of the disease.

The "prevention of cancer" includes preventing or delaying the onset of the cancer or one or more symptoms associated with said cancer. The "prevention of cancer" also refers to any act intended to ameliorate the health status of patients such as therapy, prophylaxis and retardation of the disease and/or to prevent the patient from being afflicted by the disease. In some embodiments, this term also refers to minimizing the risk (or the probability) for a patient to develop said cancer, as compared to a patient who has not been administered the compound of the invention.

As used herein, "a therapeutically effective amount or dose" refers to an amount of the compound of the invention which prevents, removes, or slows down the cancer or reduces or delays one or several symptoms or disorders caused by or associated with said disease in the subject, preferably a human. The effective amount, and more generally the dosage regimen, of the compound of the invention and pharmaceutical compositions thereof may be determined and adapted by one skilled in the art. An effective dose can be determined by the use of conventional techniques and by observing results obtained under analogous circumstances. The therapeutically effective dose of the compound of the invention will vary depending on the disease to be treated or prevented, its gravity, the route of administration, any co-therapy involved, the patient's age, weight, general medical condition, medical history, etc. Typically, the amount of the compound to be administrated to a patient may range from about 0.01 mg/kg to 500 mg/kg of body weight, preferably from 0.1 mg/kg to 300 mg/kg of body weight, for instance from 25 to 300 mg/kg. The compound or the nanoparticle of the invention may be administered to the subject daily during several consecutive days, for example during 2 to 10 consecutive days, preferably from 3 to 6 consecutive days. Said treatment may be repeated every two or three weeks or every one, two or three months. Alternatively, the compound or the nanoparticle of the invention may be administered as a single dose once a week, once every two weeks, or once a month. The treatment may be repeated one or several times per year.

The administration of the compound of the invention may be topical, parenteral or enteral. Indeed, the compound of the invention may be administered by any conventional route including, but not limited to, oral, buccal, sublingual, rectal, intravenous, intramuscular, subcutaneous, intraosseous, dermal, transdermal, mucosal, transmucosal, intra-articular, intracardiac, intracerebral, intraperitoneal, intranasal, pulmonary, intraocular, vaginal, or transdermal route. Indeed, the administration route of the compound of the invention may vary depending on the disease to treat and the organ or tissue of the patient afflicted by the disease. In some preferred embodiments, the compound of the invention is administered by intravenous route or oral route. As mentioned above, the subject or patient is preferably a human being.

In a particular aspect, the compound or the nanoparticle of the invention may be administered to the subject in combination with an additional therapeutic agent. The additional therapeutic agent may be an anticancer agent. Non-limiting examples include in particular interferons, cisplatin, bleomycin, fluorouracil, methotrexate, vincristine, actinomycin, vinorelbine, taxanes such as paclitaxel and docetaxel, or an anthracycline. Furthermore, an active ingredient for neutralizing the potential toxicity of acrolein can be administered, in particular sodium mercaptoethanesulfonate. The compound or the nanoparticle of the invention and the additional compound may be administered to the patient by the same route or by distinct routes, simultaneously, separately or successively.

The compound or the nanoparticle of the invention may be used in combination with radiotherapy.

It goes without saying that the therapeutic method and use of the invention may be implemented by administering any one of the compounds described herein, in particular compounds of formula (Ia), (Ib), (Ic), (IIa) or (IIb), preferably compound of formula (IIa) or (IIb).

In an additional aspect, the invention relates to the use of a compound of formula (I) or a nanoparticle thereof for the manufacture of a drug to be used in the treatment or the prevention of cancer or to be used in an immunosuppressive treatment.

In a further aspect, the invention relates to a pharmaceutical composition comprising a compound of formula (I) or a pharmaceutically salt or solvate thereof, a nanoparticle of the invention as well as any particular compound disclosed herein, and a pharmaceutically acceptable excipient. The compound or the nanoparticle of the invention is present as an active ingredient in said pharmaceutical composition.

The pharmaceutical composition of the invention may comprise:
  from 0.01% to 90% by weight of a compound or a nanoparticle of the invention, and
  from 10% to 99.99% by weight of pharmaceutically acceptable excipient(s), the percentage being expressed as compared to the total weight of the composition.

Preferably, the pharmaceutical composition may comprise:
  from 0.1% to 50% by weight of a compound or a nanoparticle of the invention, and
  from 50% to 99.9% by weight of pharmaceutically acceptable excipients.

Such a pharmaceutical composition is preferably to be used in the treatment or the prevention of a cancer or for providing immunosuppression.

The pharmaceutical composition of the invention may be formulated according to standard methods such as those described in Remington: The Science and Practice of Pharmacy (Lippincott Williams & Wilkins; Twenty first Edition, 2005).

Pharmaceutically acceptable excipients that may be used are, in particular, described in the Handbook of Pharmaceuticals Excipients, American Pharmaceutical Association (Pharmaceutical Press; 6th revised edition, 2009). Typically, the pharmaceutical composition of the invention may be obtained by admixing a compound of formula (I) as described above or nanoparticle thereof with at least one pharmaceutically excipient.

Examples of appropriate excipients include, but are not limited to, solvents such as water or water/ethanol mixtures, fillers, carriers, diluents, binders, anti-caking agents, plasticizers, disintegrants, lubricants, flavors, buffering agents, stabilizers, colorants, dyes, anti-oxidants, anti-adherents, softeners, preservatives, surfactants, wax, emulsifiers, wetting agents, and glidants. Examples of diluents include, without being limited to, microcrystalline cellulose, starch, modified starch, dibasic calcium phosphate dihydrate, calcium sulfate trihydrate, calcium sulfate dihydrate, calcium carbonate, mono- or disaccharides such as lactose, dextrose, sucrose, mannitol, galactose and sorbitol, xylitol and combinations thereof. Examples of binders include, without being limited to, starches, e.g., potato starch, wheat starch, corn starch; gums, such as gum tragacanth, acacia gum and gelatin; hydroxypropyl cellulose, hydroxyethyl cellulose, hydroxypropyl methylcellulose; polyvinyl pyrrolidone, copovidone, polyethylene glycol and combinations thereof. Examples of lubricants include, without being limited to, fatty acids and derivatives thereof such as calcium stearate, glyceryl monostearate, glyceryl palmitostearate magnesium stearate, zinc stearate, or stearic acid, or polyalkylene glycols such as PEG. The glidant may be selected among colloidal silica, dioxide silicon, talc and the like. Examples of disintegrants encompass, without being limited to, crospovidone, croscarmellose salts such as sodium croscarmellose, starches and derivatives thereof. Examples of surfactants encompass, without being limited to, simethicone, triethanolamine, polysorbates and derivatives thereof such as Tween® 20 or Tween® 40, poloxamers, fatty alcohol such as laurylic alcohol, cetylic alcohol and alkylsulfate such as sodium dodecylsulfate (SDS). Examples of emulsifiers, encompass for example, ethyl alcohol, isopropyl alcohol, ethyl carbonate, ethyl acetate, benzyl alcohol, benzyl benzoate, propylene glycol, 1,3-butylene glycol, dimethylformamide, oils, polyethylene glycol and fatty acid esters of sorbitan or mixtures of these substances.

It goes without saying that the excipient(s) to be combined with the active compound of the invention may vary upon (i) the physico-chemical properties including the stability of the said active compound, (ii) the pharmacokinetic profile desired for said active ingredient, (iii) the dosage form and (iv) the route of administration.

The composition of the invention may be administered by any suitable route as mentioned above. The administration route may be, without being limited to, subcutaneous, intramuscular, intravenous, oral, dermal, transdermal, pulmonary, intra-articular, intraosseus.

The pharmaceutical composition may be of any type. For instance the pharmaceutical composition may be a solid oral dosage form, a liquid dosage form, a suspension, for instance for intravenous route, a dosage form for topical application such as cream, ointment, gel and the like, a patch, such as a transdermal patch, a muco-adhesive patch or tablet, in particular adhesive plaster or bandage, a suppository, an aerosol for intranasal or pulmonary administration. In some particular embodiments, the pharmaceutical composition may be a lyophilizate or a freeze-dried powder. Said powder may be dissolved or suspended in an appropriate vehicle just before being administered to the patient, for instance by intravenous route or oral route.

Oral solid dosage forms encompass, without being limited to, tablets, capsules, pills, and granules. Optionally, said oral solid forms may be prepared with coatings and shells, such as enteric coatings or other suitable coatings or shells. Several such coatings and/or shells are well known in the art. Examples of coating compositions which can be used are polymeric substances and waxes. Liquid dosage forms include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, for example, ethyl alcohol, isopropyl alcohol, ethyl carbonate, ethyl acetate, benzyl alcohol, benzyl benzoate, propylene glycol, 1,3-butylene glycol, dimethylformamide, oils, polyethylene glycol and fatty acid esters of sorbitan or mixtures of these substances, and the like. If desired, the composition can also include adjuvants, such as wetting agents, emulsifying agents, suspending agents, anti-oxidant agents, buffers, pH modifying agents and the like. Suspensions, in addition to the compound or the nanoparticle of the invention, may contain suspending agents, such as, ethoxylated isostearyl alcohols, polyoxyethylene sorbitol and sorbitan esters, microcrystalline cellulose, aluminum metahydroxide, bentonite, agar-agar, and the like. Vaginal or rectal suppositories may be prepared by mixing the compounds of the present invention with suitable non-irritating excipients or carriers such as cocoa butter, polyethylene glycol, or a suppository wax which are solid at ordinary temperatures but liquid at body temperature and therefore, melt in the rectum or vaginal cavity and release the active component. The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

In some further embodiments, the composition may comprise another active ingredient such as an anticancer agent, in particular as described above, or a compound to prevent potential side effects such as sodium mercaptoethanesulfonate.

Other aspects of the present invention are illustrated in the following examples, which are only illustrative in nature, but do not limit the scope of this application.

Example 1: Preparation of IFO Derivatives

The synthesis of some pre-activated conjugates of ifosfamide is depicted in the scheme below:

a: RY = C₅H₁₁O b: RY = c: RY =

4-methoxy-ifosfamide (4-MeO-IFO, 1) was prepared by anodic oxidation of ifosfamide in methanol as described in Paci et al., 2001, Bioorg Med Chem Lett, 11, 1347-1349. The substitution of the methoxy group by the relevant alkyl chains took advantage of the formation of the iminium salt upon Lewis acid treatment of 4-MeO-IFO.

Briefly, to a stirring solution of 4-MeO-IFO (2) (200 mg, 0.68 mmol) in anhydrous $CH_2Cl_2$ (10 mL) was added dropwise $BF_3.OEt_2$ (172 µL, 0.68 mmol) at −78° C. After 45 minutes, a solution of RYH (210 mg, 1.37 mmol) in $CH_2Cl_2$ (0.5 mL) was added dropwise, the mixture was stirred for an additional 1 h at −78° C. and quenched by addition of 10 mL of a saturated $Na_2CO_3$ solution. After extraction with $CH_2Cl_2$ (3×20 mL), the combined organic phases were dried over $MgSO_4$ and concentrated under reduced pressure. The obtained residue was purified by column chromatography.

Geranyloxy-IFO (3b):

RYH=geraniol

Purification: silica gel, $CH_2Cl_2$:$(CH_3)_2CO$:$Et_3N$ (95:5:0.5, v:v:v)

Yellow oily residue obtained (80 mg, yield 25%)

NMR in $CD_3)_2CO$:

³¹P δ(ppm): 8.5

¹³C δ(ppm): 16.7 ($C_{18}$ or $C_{19}$); 17.8 ($C_{18}$ or $C_{19}$); 25.9 ($C_{20}$); 27.1 ($C_{14}$ or $C_{15}$); 31.1 ($C_5$); 40.23 ($C_{14}$ or $C_{15}$); 43.6 ($C_7$); 44.1 ($C_8$); 46.5 ($C_{10}$); 50.1 ($C_9$); 63.3 ($C_6$); 64.9 ($C_{11}$); 88.8 ($C_4$); 121.7 ($C_{12}$ or $C_{16}$); 124.8 ($C_{12}$ or $C_{16}$); 131.8 ($C_{17}$); 140.7 ($C_{13}$).

¹H δ(ppm): 1.35 (d, 1H, J=14 Hz, $H_{5\alpha}$), 1.60 (s, 3H, $H_{18}$ or $H_{19}$), 1.66 (s, 3H, $H_{18}$ or $H_{19}$), 1.78 (s, 3H, $H_{20}$), 1.85 (m, 1H, $H_{5\beta}$), 2.11 (m, 2H), 2.22 (m, 2H), 3.05 (m, 1H, $H_{9\alpha}$), 3.17 (m, 2H, $H_7$), 3.33 (m, 2H), 3.73 (m, 5H), 3.84 (m, 2H, $H_{6\alpha}$), 4.21 (m, 1H, $H_{6\beta}$), 4.30 (dd, 1H, J=4 and 21 Hz, $H_5$), 5.26 (m, 1H, $H_{12}$ or $H_{16}$), 5.42 (m, 1H, $H_{12}$ or $H_{16}$).

MS (+ESI): m/z (%) 413.2 (100) [M+H]⁺; 415.2 (65) [M+2+H]⁺.

HRMS (+ESI): m/z 413.1524 ([M+H]⁺ calcd for $C_{36}H_{60}Cl_2N_3O_3PS$:413.1527).

Pentyloxy-IFO (3a)

RYH=pentanol

Purification: silica gel, $CH_2Cl_2$:$(CH_3)_2CO$:$Et_3N$ (95:5:0.5, v:v:v)

Yellow oil (90 mg, yield 33%)

¹H NMR (($CD_3)_2CO$ 400 MHz): δ 0.92 (t, 3H, J=7.1 Hz, $O(CH_2)_4CH_3$), 1.30-1.45 (m, 4H, $CH_3CH_2CH_2$), 1.62 (m, 2H, $OCH_2CH_2$), 2.02-2.07 (m, 3H, $H_5$ and NH), 3.16-3.30 (m, 2H, $OCH_2CH_2$), 3.47-3.55 (m, 4H, $NCH_2CH_2Cl$ and $NHCH_2CH_2Cl$) 3.60-3.65 (m, 2H, $NCH_2CH_2Cl$), 3.70-3.75 (m, 2H, $NHCH_2CH_2Cl$), 4.05-4.20 (m, 1H, $H_6$), 4.35-4.50 (m, 1H, $H_6$), 4.70-4.80 (dd, 1H, J=20.5 Hz and J=2.9 Hz, $H_4$) ppm.

¹³C NMR (($CD_3)_2CO$ 100 MHz): δ 14.3 ($CH_3$, $O(CH_2)_4CH_3$), 23.2 ($CH_2$, $O(CH_2)_3CH_2CH_3$), 29.3 ($CH_2$, $O(CH_2)_2CH_2CH_3$), 30.4 ($CH_2$, $OCH_2CH_2(CH_2)_2CH_3$), 30.9 ($CH_2$, $C_5$), 43.6 ($CH_2$, $NCH_2CH_2Cl$), 44.0 ($CH_2$, $NHCH_2CH_2Cl$), 46.6 ($CH_2$, $NHCH_2CH_2Cl$), 50.2 ($CH_2$, $NCH_2CH_2Cl$), 63.2 ($CH_2$, $C_6$), 68.6 ($CH_2$, $OCH_2(CH_2)_3CH_3$), 89.8 (CH, $C_4$) ppm.

³¹P NMR (($CD_3)_2CO$ 160 MHz): δ 7.60 (s) and 8.46 (s).

MS (+ESI): m/z (%) 347.1 (100) [M+H]⁺; 349.1 (70) [M+2+H]⁺.

HRMS (+ESI): m/z 347.1049 ([M+H]⁺ calcd for $C_{12}H_{25}Cl_2N_2O_3P$: 347.1058).

13,17-Dimethyloctyloxy-IFO (3c)

RYH=3,7-dimethyloctanol
Purification: silica gel, $CH_2Cl_2$:$(CH_3)_2CO$:$Et_3N$ (95:5:0.5, v:v:v)
Brown oily residue (90 mg, yield 28%)
$^1$H NMR (($CD_3$)$_2CO_3$ 400 MHz): δ 0.74 (m, 9H, O($CH_2$)$_2$CH($CH_3$)($CH_2$)$_2$CH($CH_3$)$_2$), 1.05-1.20 (m, 4H, ($CH_2$)$_2$CH($CH_3$)$_2$), 1.60-1.70 (m, 2H, $NCH_2CH_2Cl$), 2.01-2.07 (m, 2H, $H_6$), 2.91 (s, 1H, NH), 3.15-3.30 (m, 4H, $NCH_2CH_2Cl$ and $NHCH_2CH_2Cl$), 3.45-3.60 (m, 4H, $NCH_2CH_2Cl$ and $NHCH_2CH_2Cl$), 3.64 (m, 2H, $H_{11}$), 4.05-4.19 (m, 1H, $H_5$), 4.35-4.50 (m, 1H, $H_5$), 4.70 (m, 1H, $H_4$).
$^{13}$C NMR (($CD_3$)$_2CO_3$ 100 MHz): δ 20.0 ($CH_3$, CH($CH_3$)$_2$), 23.0 ($CH_3$, CH($CH_3$)$_2$), 25.4 ($CH_3$, $CH_2CH(CH_3)$), 28.7 ($CH_3$, $CH_2(CH_2)_2CH(CH_3)_2$), 30.5 ($CH_2$, $C_5$), 40.0 ($CH_2$, $NHCH_2CH_2Cl$), 43.6 ($CH_2$, $CH_2CH_2CH(CH_3)_2$), 44.0 ($CH_2$, $NCH_2CH_2Cl$), 46.7 ($CH_2$, $NCH_2CH_2Cl$), 49.7 ($CH_2$, $OCH_2CH_2CH(CH_3)$), 50.3 ($CH_2$, $NHCH_2CH_2Cl$), 63.2 ($CH_2$, $C_6$), 66.7 ($CH_2$, $OCH_2CH_2CH(CH_3)$), 89.8 (CH, $C_4$) ppm. $^{31}$P NMR (($CD_3$)$_2CO_3$ 160 MHz): δ 8.47 (s) and 7.55 (s) ppm.
MS (+ESI): m/z (%) 417.2 (100) [M+H]$^+$; 419.2 (70) [M+2+H]$^+$.
HRMS (+ESI): m/z 417.1839 ([M+H]$^+$ Calcd for $C_{36}H_{62}Cl_2N_3O_3PS$:417.1840).

Example 2: Preparation of Supramolecular Nano-Assemblies (Nanoparticles) (NAs)

Materials and Methods
Nano-assemblies (NAs) from prodrugs Geranyloxy-IFO (3b) at a concentration of 2 mg/mL and 5 mg/ml, were prepared in a single step by nanoprecipitation of solution (8 mg/mL in acetone) in milliQ® water (ratio acetone:water 1:4; v:v). Formation of NAs occurred immediately without the use of any surfactant. The organic solvent was then evaporated at room temperature under vacuum using a Rotavapor® and the organic solvent-free colloidal dispersions were stored at 4° C.
The hydrodynamic diameter of the NAs was measured at 20° C. by Dynamic Light scattering using a Nanosizer ZS (Malvern Instrument Ltd, France). An amount of 20 μL of the suspension was diluted in 980 μL of Milli-Q water. The results give the mean hydrodynamic diameter of the dispersed NAs from three independent series of ten measurements. The standard deviation and the polydispersity index were also given.
The Zeta (ξ) potential was also determined by dilution of 20 μL of the suspension in 980 μL of a 1 mom Nail solution using a Nanosizer ZS (Malvern Instrument Ltd, France).
Results
Geranyloxy-IFO gave satisfactory NAs, in spite of its short two-isoprene unit appendage. No surfactant was needed to obtain such nanoparticles. The resulting nanoparticles that exhibited the characteristic Tyndall effect of colloidal systems had a polydispersity index of about 0.10-0.20 as measured by quasi-elastic light scattering. The mean diameter of the obtained NAs was between 150 nm and 220 nm. Interestingly, the nanoparticles displayed high drug loading (63.1%).
The nanoparticles were stable under storage as no significant change in their size was detected over a three day storage period at 4° C. The colloidal stability of geranyloxy-IFO could be correlated with its negative Zeta potential. Furthermore, this highly hydrolysable compound was found chemically unchanged by $^1$H NMR and by MS after 24 h. This result seemed to indicate that within the NAs, the polar headgroup of geranyloxy-IFO was protected from the external aqueous medium and thus from hydrolysis.
Noteworthy, pentyloxy-IFO (3a) and 13,17-Dimethyloctyloxy-IFO (3c) did not provide any suspension of nanoparticles, which clearly demonstrates that the geranyloxy radical as a terpene played a crucial role for promoting self-assembling.

TABLE 1

Physico-chemical characteristics of the NAs of geranyloxy-IFO

| Concentration (mg/ml) | Mean diameter (nm) | Polydispersity Index (PdI) | Zeta potential (mV) | Drug Loading (%) |
| --- | --- | --- | --- | --- |
| 2 | 166.0 +/− 18.0 nm | 0.114 +/− 0.016 | −30 | 63.1 |
| 5 | 208.7 +/− 13.1 nm | 0.201 +/− 0.010 | −13 | |

Noteworthy enough, the mean diameter and the drug loading obtained for geranyloxy-IFO nanoparticles are similar to those observed for IFO derivatives substituted by squalenoyl radical (SQ) such as SQ-IFO (mean diameter: 147 nm and drug loading: 40.4%) and SQ-thio-IFO (mean diameter: 170 nm and drug loading: 36.3%) described in WO2012/076824.

Figure 1:
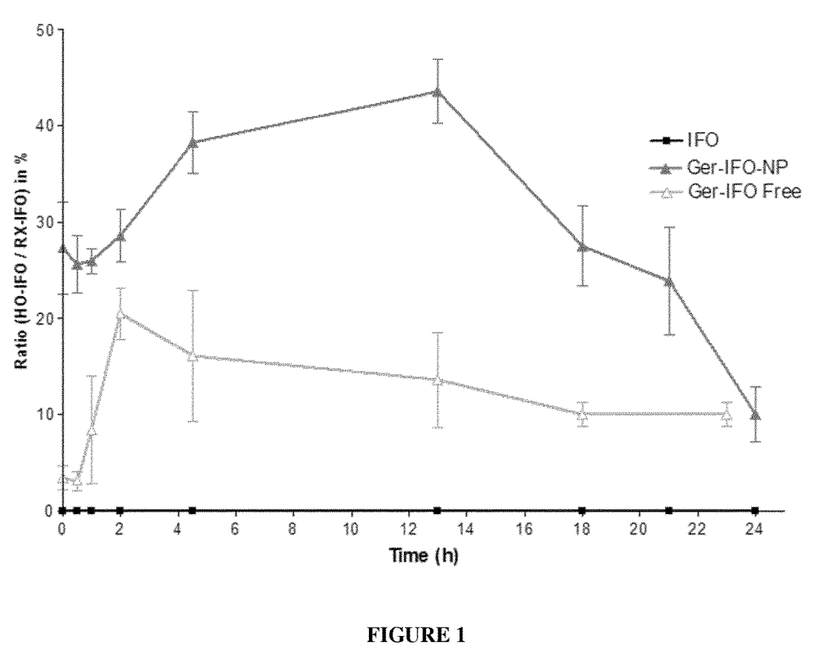
FIG. 1 shows the ratio of 4HO-IFO/geranyloxy-IFO as a function of time in mice plasma. The release of 4-OH-IFO was up to 20% for Geranioxy-IFO as free form (Ger-IFO-NP) and up to 45% for geranyloxy-IFO nanoparticles (Ger-IFO-NP). By contrast, IFO does not release 4-OH-IFO in these ex vivo conditions.

Example 3: In Vitro Release of 4-Hydroxy-Ifosfamide (4-HO-IFO) from Geranyloxy-IFO The kinetic study of the 4-HO-IFO release from geranyloxy-IFO (in free form or in nanoparticle form) was performed over 24 h in mouse plasma (c=10 μg/mL) incubated at 37° C. The concentrations of 4-HO-IFO and geranyloxy-IFO were assessed in mice plasma using a quantitative HPLC-MS/MS assay and allowed to display the release yield, expressed as the (4-HO-IFO/geranyloxy-IFO) ratio. IFO (without CYP-activation) was used as negative control. As illustrated by FIG. 1 which shows the HO-IFO/geranyloxy ratio upon time, 4-HO-IFO metabolite was released from geranyloxy-IFO nanoparticles or geranyloxy-IFO in free form without activation by cytochromes.

Example 4: Evaluation of In Vitro Cytotoxicity

Materials and Methods:
The compounds (3a-c) pentyloxy-, dimethyloctyloxy- and geranyloxy-IFO were tested on two cancerous cell lines namely, A673 (human Ewing Sarcoma cell line) and RMS-1 cell line using MTS ((3-(4,5-dimethylthiazol-2-yl)-5-(3-carboxymethoxyphenyl)-2-(4-sulfophenyl)-2H-tetrazolium)) (Promega) method. Pentyloxy-IFO and dimethyloctyloxy-IFO were tested under free form as these compounds do not form nanoparticles. Geranyloxy-IFO compound was tested in bulk form and in nanoparticle form (see Example 2). The experiments were conducted in the absence of cytochrome. Ifosfamide (IFO), geraniol, pentanol and 3,7-dimethyloctanol was used as negative controls.

The cells were seeded in 96-well plates at optimal cell density determined previously and incubated with 100 µL of DMEM or RPMI containing 10% of FBS and 100 U/mL penicillin and 100 µg/mL streptomycin at 37° C., 5% $CO_2$ in moist atmosphere. After 24 h, the cells were treated with 100 µL of the different pre-activated prodrugs at different concentrations:
 −0.1, 0.5, 1, 5, 10, 50, 100, 200 µM for A673 cell line and 0.01, 0.05, 0.1, 0.5, 1, 5, 10, 50 µM for RMS-1 cell line.

After 72 h, or 96 h for the compound Dimethyloctyloxy-IFO, 20 µL (1/10) of MTS reagent were added in each well. Depending on the cell line, 2 to 5 h incubation are needed to obtain the optimum optical density which was measured at 490 nm wavelength using a microplate reader (EL808, Biotek Instrument). Untreated cells were used as control. Each compound concentration was tested in six replicates. Results show the percentage of living cells compared to the control, and the $IC_{50}$ of each compound regarding the tested cell line was determined using Prism 4 (Graph Pad Software, San Diego).

Results

The $IC_{50}$ obtained for each cell line for the tested compounds are shown in Table 2 below:

|  | In vitro Activity (IC50 µM) | |
| --- | --- | --- |
| Compounds | A673 | RMS-1 |
| IFO | >200 | >50 |
| Geraniol | >200 | >50 |
| Pentanol | >200 | >500 |
| 3,7-dimethyloctanol | >200 | >50 |
| Pentyloxy-IFO (3a) | 17.7 ± 2.3 | 5.3 ± 1.7 |
| 13,17-Dimethyloctyloxy-IFO (3c) | >200 | >50 |
| 13,17-Dimethyloctyloxy-IFO (3c)** | 24.5 ± 2.1 | 11.3 ± 5.8 |
| Geranyloxy-IFO (bulk) (3b) | 25.3 ± 1.5 | 9.3 ± 4.2 |
| Geranyloxy-IFO (nanoparticles) (3b) | 14.7 ± 5.0 | 0.6 ± 0.2 |

* 72 h incubation
**(96 h incubation)

Figure 2:
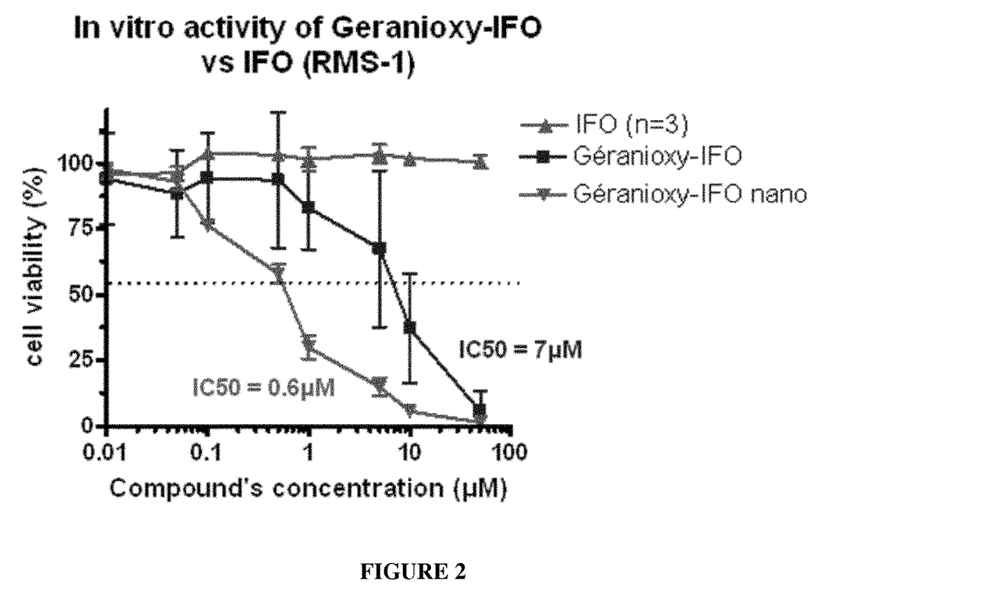
FIG. 2 shows the in vitro cytotoxicity of IFO, geranyloxy-IFO (Géranioxy-IFO) in bulk form and geranyloxy-IFO nanoparticles (Géranioxy-IFO nano) in RMS-1 cells after an incubation of 72 hours. X-axis: Concentration in μM (log scale). Y-axis: percentage of cell viability.

The results obtained for RMS-1 cell line are also depicted in FIG. 2.

As expected, in the absence of cytochrome, IFO did not exhibit significant cytotoxicity at the concentrations tested. The same results were observed for geraniol, pentanol and 3,7-dimethyloctanol.

By contrast, Geranyloxy-IFO displays a significant cytotoxicity toward A673 and RMS-1, in the absence of cytochrome. Thus, this compound is capable of releasing the alkylating mustard without prior activation by cytochrome P450. Surprisingly, the cytotoxicity of Geranyloxy-IFO is significantly increased when formulated as nanoparticles. Indeed, Geranyloxy-IFO in nanoparticle form was two-fold (A673 cell line) and 15-fold (RMS-1 cell line) more active as than Geranyloxy-IFO in free form with $IC_{50}$ of 14.7 and 0.6 µM, respectively (Table 2).

Noteworthy, 13,17-Dimethyloctyloxy-IFO, which is structurally close to geranyloxy-IFO, did not exhibit significant cytotoxicity after an incubation of 72 h on the tested cells but provides similar cytotoxicity when incubated with cells during 96 h. Such a result demonstrates the impact of geranyloxy radical on cytotoxicity potential of the compounds. Moreover, the $IC_{50}$ for geranyloxy-IFO nanoparticles for A673 and RMS cell lines were lower than those of SQ-IFO ($IC_{50}$: 22.0±5.0 and 11.4±5.0 µM) and SQ-thio-IFO nanoparticles ($IC_{50}$: 23.2±1.3 and 33.0±1.8 µM).

Example 5: Evaluation of Anti-Tumor Effect In Vivo

In vivo cytotoxic efficacy was evaluated first on a model of human rhabdomyosarcoma xenografted in nude mice. The model used is RD cell line. The cells were first amplified in culture and counted. Cells were injected subcutaneously in both flanks of each mouse. After graft uptake, the mice divided into 4 groups of 7 mice:
 Group 1: the mice received vehicle (placebo) (DMSO/water 3/7 with 9% of NaCl);
 Group 2: the mice were administered with a single dose of 300 mg/kg of IFO (solution of 37.5 mg/ml of IFO in vehicle);
 Group 3: the mice were administered with a single dose of 158 mg/kg of geranyloxy-IFO (solution of 19.7 mg/ml of geranyloxy-IFO in vehicle), equivalent to 100 mg of IFO; and
 Group 4: the mice were administered with a single dose of 59 mg/kg geraniol (solution of 7.4 mg/ml of geraniol in vehicle) equivalent to 59 mg of IFO.

The administration was performed by intravenous route at day 0. Geranyloxy-IFO was administered as free form.

Results

Figure 3:
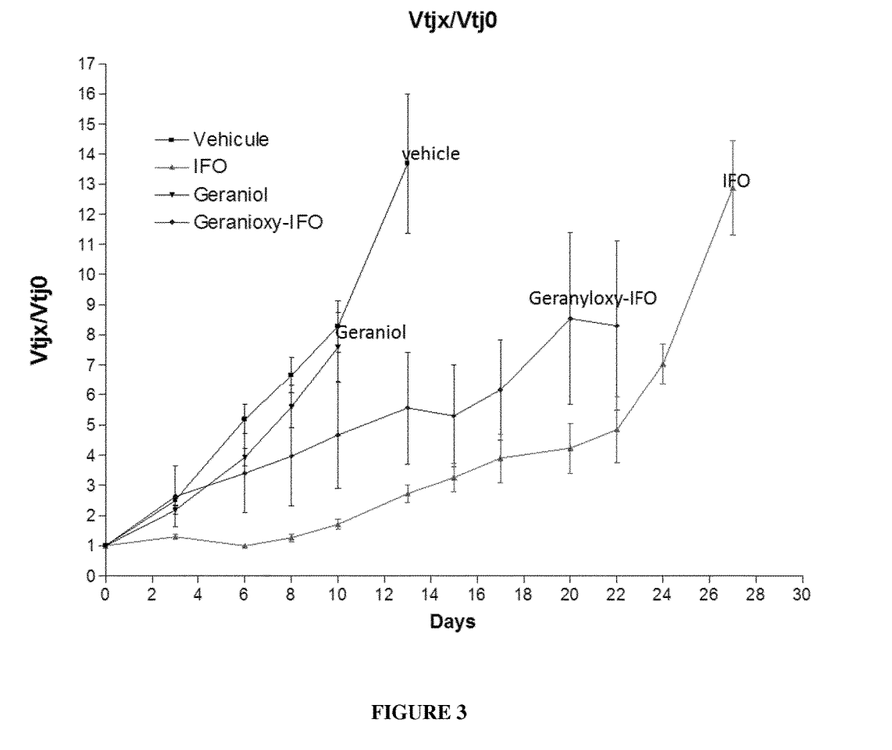
FIG. 3 shows the growth of tumor in mice xenografted with RD tumor. The mice were intravenously administered with placebo (vehicle), Geranyloxy-IFO (158 mg/kg equivalent to 100 mg/kg of IFO), geraniol (59 mg/kg) or IFO (300 mg/kg) as a unique dose, at day 0, by intravenous route. X-axis: day of post-administration, Y-axis: ratio of the "tumor volume at day+J" to the "tumor volume at day 0" (Vtjx/Vtj0).

The results are shown in FIG. 3, which illustrates for each group, the tumor growth as a function of time. The proof of principle was demonstrated as a single dose of 158 mg/kg of Geranyloxy-IFO (which is equivalent to 100 mg/kg of IFO) showed antitumor activity, in terms of tumor volume growth as shown for IFO at 300 mg/kg. No tumor growth inhibition was found for vehicle or geraniol.

Example 6: Pharmacokinetics and Metabolization of Geranyloxy-IFO In Vivo 28 nude mice were divided into 3 groups:
 Group 1 (4 mice): the mice were intraperitoneally administered with 200 µl of a vehicle (placebo) (water+5% glucose);
 Group 2 (12 mice): the mice were intraperitoneally administered with a dose of 25 mg/kg of IFO (10.4 mg/ml in vehicle); and
 Group 2 (12 mice): the mice were intraperitoneally administered with a dose of 40 mg/kg (25 mg/kg equivalent IFO) of IFO (16.5 mg/ml in vehicle).

Plasma samples from each mouse were performed at 5, 15, 30 and 60 minutes after administration. The plasma concentrations of the drugs (IFO or geranyloxy-IFO) and metabolites (4-HO-IFO and N-dechlorethyl metabolites) were determined in each plasma sample.

Results

Figure 4:
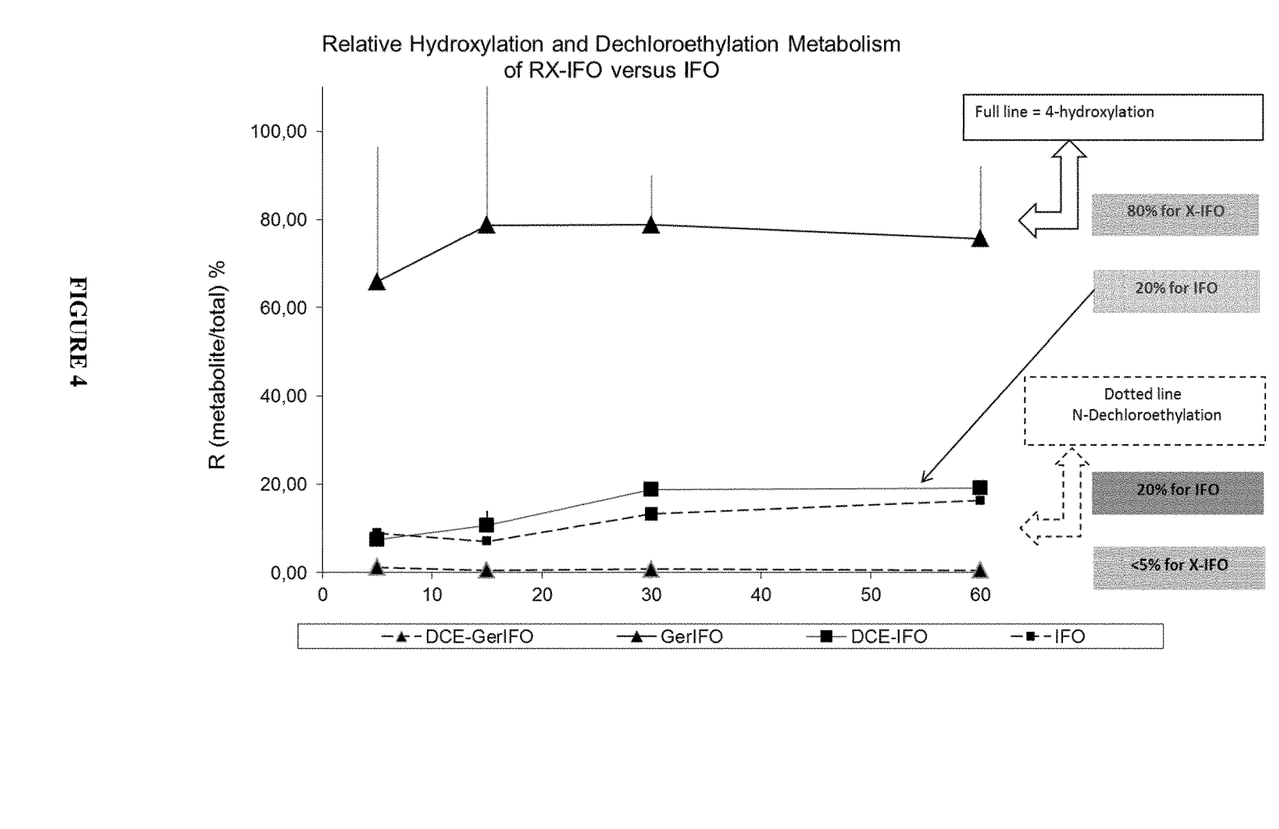
FIG. 4 shows the conversion of Geranyloxy-IFO and IFO into 4 HO-IFO and dechloroethyl metabolites in vivo in mice. X-axis: time after intravenous administration. Y-axis: percentage of conversion (metabolites detected in mice plasma).

The results are shown in FIG. 4. Geranyloxy-IFO is rapidly converted into pre-active 4-HO-IFO metabolite. The conversion rate of Geranyloxy-IFO (GerIFO) into 4-HO-IFO is about 80% at 20 minutes post-administration. Noteworthy enough, the metabolization of IFO does not produce significant amount of into N-dechlorethyl metabolites (DCE-GerIFO), which account for less than 1%. Such a result illustrates that Geranyloxy-IFO is not significantly metabolized by CYP2B6. Thus, the release of neuro- and nephro-toxic chloroacetaldehyde may be significantly lower than that for IFO, for which N-dechlorethyl metabolites (DCE-IFO) account for about 15%. It is thus expected that geranyloxy-IFO displays a good therapeutic efficacy at lower doses and with less side effects than IFO.

Example 6: Synthesis of Geranyloxy-Cyclophosphamide 4-geranyloxy-cyclophosphamide was prepared by anodic oxidation of cyclophosphamide into 4-methoxy-cyclophosphamide (4-MeO-CPO) followed by nucleophile substitution by geraniol in the presence of a Lewis acid.

Briefly, in an electrolysis cell, cyclophosphamide (300 mg) and sodium tetrafluoroborate (190 mg) were dissolved in methanol (10 ml). After subjecting the mixture to a current of 2 faradays by mole of cyclophosphamide with an intensity of 10 mA, the reaction medium was evaporated in the presence of sodium carbonate. The residue was taken up in dichloromethane (10 ml), under inert atmosphere and stirring. One equivalent of $BF_3.OEt_2$ was added dropwise at $-50°$ C. After one hour of stirring at low temperature, 2 equivalents of geraniol were added dropwise. The mixture was stirred for an additional 1 hour at low temperature. After concentration of the organic phase, the resulting residue is purified by chromatography with dichloromethane/acetone 990/10 as eluent.

Molecular weight: 413.32 g·mol$^{-1}$
Chemical formula: $C_{17}H_{31}Cl_2N_2O_3P$
NMR $(CD_3)_2CO$: $^{31}P$: 7.27 and 7.32 ppm.
$^{13}C$: δ 16.7 ($CH_3$, $C_{19}$), 17.8 ($CH_3$, $C_{20}$), 25.9 ($CH_3$, $C_{18}$), 27.2 ($CH_2$, $C_{15}$), 31.7 ($CH_2$, $C_5$), 40.3 ($CH_2$, $C_{14}$), 43.2 ($CH_2$, $C_8$ and $C_{10}$), 44.9 ($CH_2$, $C_7$ and $C_9$), 63.7 ($CH_2$, $C_8$ and $C_{11}$), 82.5 (CH, $C_4$), 122.3 (CH, $C_{12}$), 125.0 ($C_{16}$), 132.0 (C, $C_{17}$), 139.8 (C, $C_{13}$) ppm.

$^1H$: δ 1.60 (s, 3H, HC=C($CH_3$)), 1.63 (s, 3H, HC=C($CH_3$)$_2$), 1.66 (s, 3H, HC=C($CH_3$)$_2$), 1.77-1.83 (m, 1H, $H_{5\alpha}$), 2.08-2.16 (m, 3H), 3.36-3.47 (m, 4H, NHCH$_2$CH$_2$Cl), 3.63-3.74 (m, 4H, NCH$_2$CH$_2$Cl), 4.04-4.10 (m, 2H, OCH$_2$CH=CH($CH_3$)), 4.60-4.70 (m, 1H, $H_6$), 4.76-4.80 (dt, 1H, J=20.9 Hz and J=3.2 Hz, $H_4$), 5.01-5.06 (1H, NH), 5.08-5.10 (tt, 1H, J=1.2 Hz and J=6.8 Hz, CH=C($CH_3$)$_2$), 5.33-5.40 (td, 1H, J=1.2 Hz and J=6.6 Hz, OCH$_2$CH=C($CH_3$)).

MS (+ESI): m/z 413 [M+H]$^+$; 435 [M+H+Na]$^+$.

Example 7: Synthesis of Geranyl Derivatives of Ifosfamide or Cyclophosphamide Comprising a Spacer Moiety Other compounds of formula (I)

can be prepared from the 4-methoxy-derivative:

by reaction with a Lewis acid so as to form the corresponding iminium, which is subsequently trapped by an appropriate nucleophile RAH in which R is the geranyl group and A is a spacer.

The table below shows some appropriate spacers A, and the corresponding nucleophiles RAH:

| No. | Spacer | RAH |
|---|---|---|
| 1 | ⁓N(R″)−CH$_2$CH$_2$−[X]$_n$⁓ | geranyl-N(R')−CH$_2$CH$_2$−[X]$_n$H |
| 2 | ⁓O−C(=O)−N(R″)−CH$_2$CH$_2$−[X]$_n$⁓ | geranyl-O−C(=O)−N(R')−CH$_2$CH$_2$−XH |
| 3 | ⁓O−C(=S)−S⁓ | geranyl-O−C(=S)−SH |

R″ is H or an alkyl group (for instance $C_1$-$C_3$ alkyl) and X is O or S.

The nucleophile RAH (1) can be obtained from geraniol according to the following synthesis:

For implementing these synthesis, one can refer to Onajole, European Journal of Medicinal Chemistry, 2010, 45, 5, 2075-2079.

RAH (2) can be obtained as follows:

For examples, one can refer to the following references: Journal of the Chemical Society Perkin Transactions, 1985, 9, 1961-6 for step (1) and Hurevich Journal of Peptide Science, 2010, 16, (4), 178-185 for step (2).

For the synthesis of RAH (3), one can refer to Synthetic Communications, 1990, 20 (5), 625-632.

The invention claimed is:

1. A compound of formula (I):

(I)

wherein:

A is selected from the group consisting of:
O, S, —O—(C=S)—S—, —ONH—, —ONR'—, —NR'O—, —NHO—, $Y_1$—$(CH_2)_n$—$Y_2$, where n is an integer from 1 to 8, and $Y_1$—$(CH_2—CH_2—O)_a$—$CH_2$—$CH_2$—$Y_2$ where a is an integer from 1 to 5, wherein $Y_1$ and $Y_2$ are independently selected from —O—, —NH—, —S—, —OC(O)—, —C(O)NH—, —NHC(O)—, —O—C(S)—S—, S—C(S)—O—NR'—, —ONH—, —NHO—, —ONR'—, —NR'O—, —OC(O)—O—, NR'C(S)S—, —SC(S)NR'—, —NR'C(O)—, —C(O)NR'— and —C(O)O—, and R' is a $C_1$-$C_6$ alkyl, and wherein —$R_1$, $R_2$ and $R_3$ are independently selected from the group consisting of —H, —CH($CH_3$)—$CH_2$—X and —$(CH_2)_2$—X, X being a halogen atom, or a pharmaceutically acceptable salt or solvate thereof.

2. A compound selected from the group consisting of:

(IIa)

(IIb)

and pharmaceutically acceptable salts thereof.

3. A pharmaceutical composition comprising a compound as an active ingredient and a pharmaceutically acceptable excipient, wherein the compound is:

(IIa)

or (IIb)

,

* * * * *

UNITED STATES PATENT AND TRADEMARK OFFICE
CERTIFICATE OF CORRECTION

PATENT NO. : 10,098,901 B2
APPLICATION NO. : 15/310455
DATED : October 16, 2018
INVENTOR(S) : Angelo Paci et al.

Page 1 of 1

It is certified that error appears in the above-identified patent and that said Letters Patent is hereby corrected as shown below:

In the Specification

Column 2,
Lines 34-35, "-O-NR'-, -NHO-," should read -- -O-NR'-, -NR'O-, -NHO-,--.

Column 6,
Lines 55-56, "-O-C(S)-S-, -ONH-, -OC(O)-O-," should read -- -O-C(S)-S-, -NR'-, -ONH-, -ONR'-, -OC(O)-O-,--.

Column 14,

Lines 54-62, "  " should read --  --.

Column 15,
Line 58, "($C_{14}$ or $C_{is}$)" should read --($C_{14}$ or $C_{15}$)--.
Line 59, "64.9 ($C_{ii}$)" should read --64.9 ($C_{11}$)--.

Column 16,
Line 62, "(($CD_3$)$_2$$CO_3$ 160" should read --(($CD_3$)$_2$CO, 160--.

Signed and Sealed this
First Day of October, 2019

Andrei Iancu
*Director of the United States Patent and Trademark Office*